(12) United States Patent
Gulla et al.

(10) Patent No.: US 7,144,554 B1
(45) Date of Patent: Dec. 5, 2006

(54) ULTRA LOW VOLUME PROBE

(75) Inventors: Gregory Gulla, Reno, NV (US); Jon E. Frudden, Reno, NV (US)

(73) Assignee: Hamilton Company, Reno, NV (US)

( * ) Notice: Subject to any disclaimer, the term of this patent is extended or adjusted under 35 U.S.C. 154(b) by 364 days.

(21) Appl. No.: 10/211,791

(22) Filed: Aug. 2, 2002

(51) Int. Cl.
*B01L 3/02* (2006.01)

(52) U.S. Cl. .................. 422/100; 73/863.32; 73/864

(58) Field of Classification Search ........... 422/100; 73/863.32, 864
See application file for complete search history.

(56) References Cited

U.S. PATENT DOCUMENTS

| | | | | |
|---|---|---|---|---|
| 4,539,855 | A * | 9/1985 | Jacobs | 73/864.25 |
| 6,197,261 | B1 * | 3/2001 | Linville et al. | 422/104 |
| 6,406,670 | B1 * | 6/2002 | Earley et al. | 422/99 |
| 6,485,692 | B1 * | 11/2002 | Freitag et al. | 422/130 |
| 6,506,611 | B1 * | 1/2003 | Bienert et al. | 436/180 |
| 6,589,483 | B1 * | 7/2003 | Maeda | 422/100 |
| 6,610,253 | B1 * | 8/2003 | Kennedy et al. | 422/100 |
| 6,756,232 | B1 * | 6/2004 | Schermer et al. | 436/180 |
| 2001/0008615 | A1 * | 7/2001 | Little et al. | 422/102 |
| 2001/0044157 | A1 * | 11/2001 | Shaion et al. | 436/180 |
| 2002/0173048 | A1 * | 11/2002 | Nakazawa et al. | 436/180 |
| 2002/0176805 | A1 * | 11/2002 | Han-Oh et al. | 422/100 |
| 2003/0017604 | A1 * | 1/2003 | Hitch et al. | 436/43 |
| 2003/0124735 | A1 * | 7/2003 | Nanthakumar et al. | 436/180 |

* cited by examiner

*Primary Examiner*—Brian R. Gordon
(74) *Attorney, Agent, or Firm*—Bernhard Kreten; Audrey A. Millemann; Weintraub Genshlea Chediak

(57) ABSTRACT

A probe head used in robotic assays for transferring liquid in miniscule quantities. The probe head includes an array of liquid transferring needles which move as a unit with the probe head. As the needles contact a surface, high spots or other irregularities on the surface are accommodated by needle compliance to assure all needles ultimately touch the surface. Touching contact assures reliable liquid transfer.

2 Claims, 3 Drawing Sheets

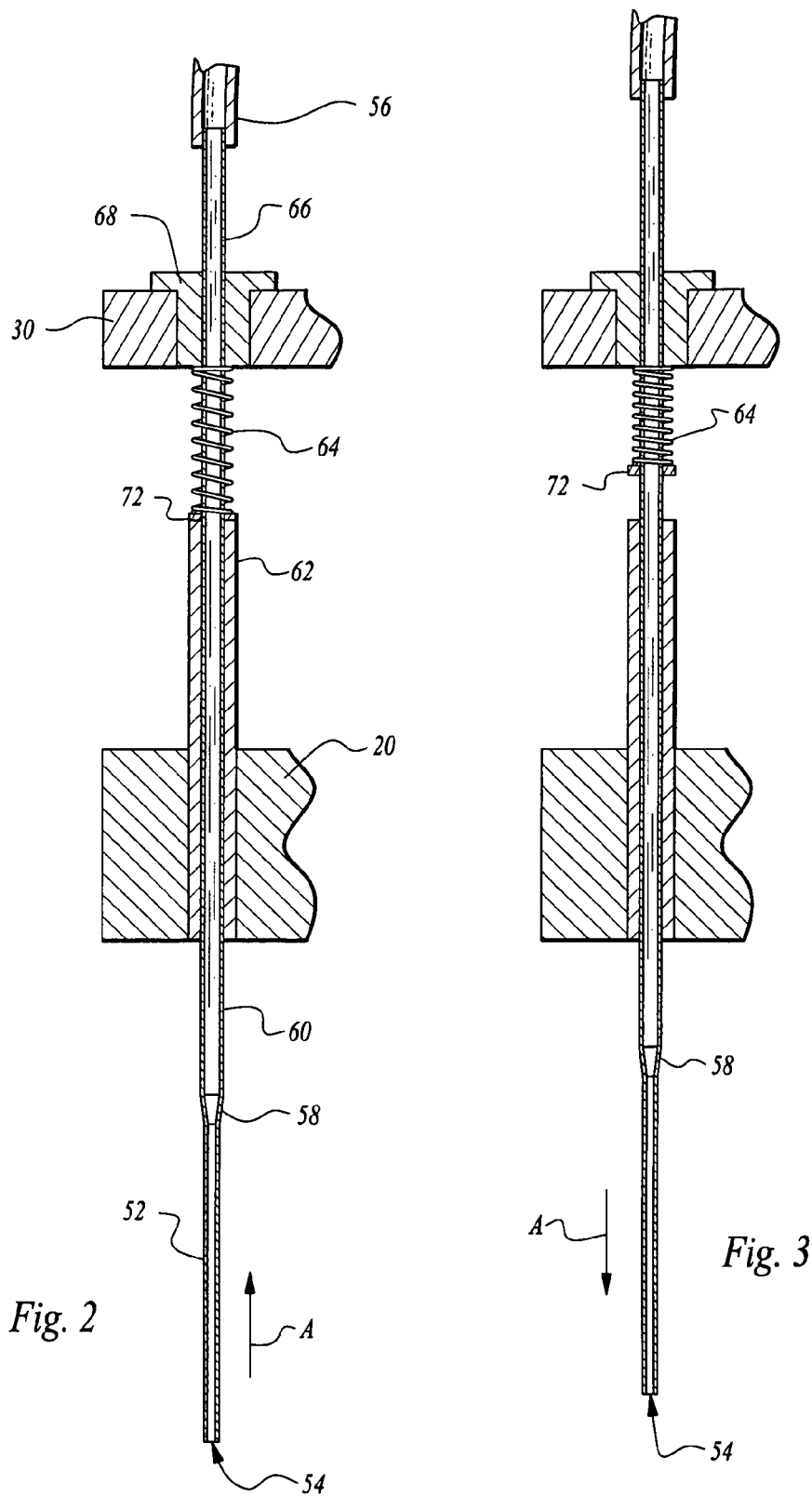

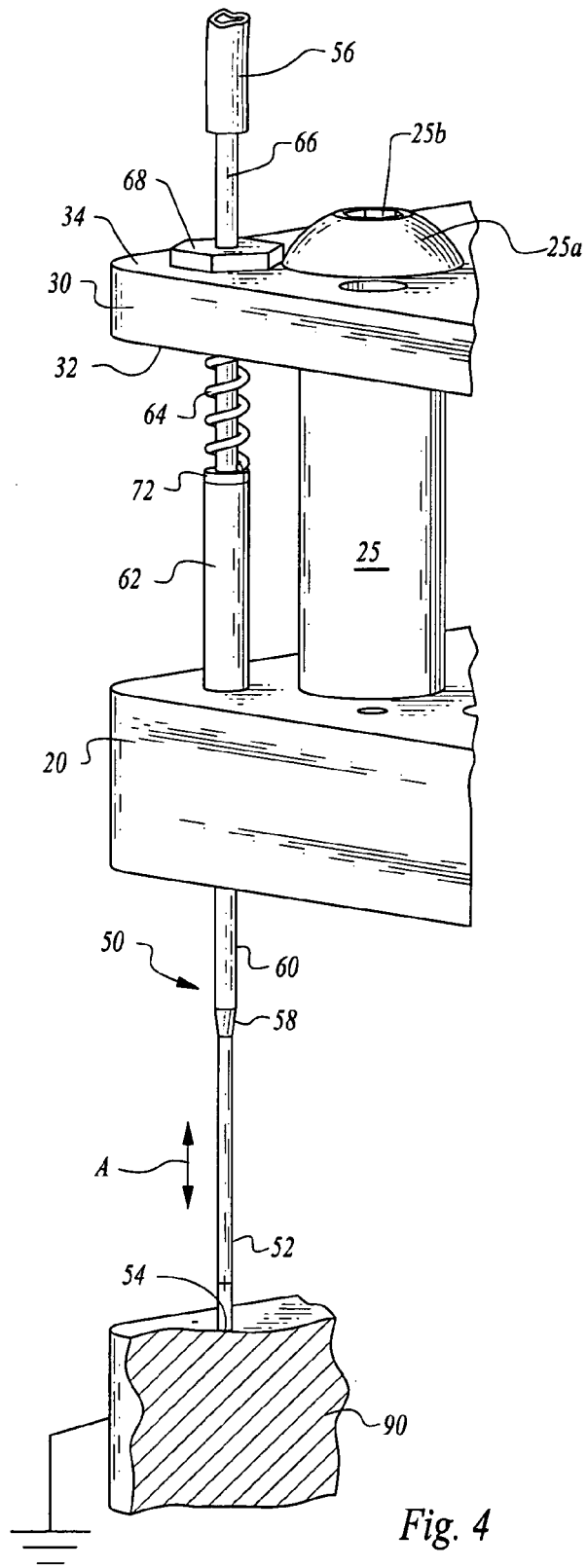
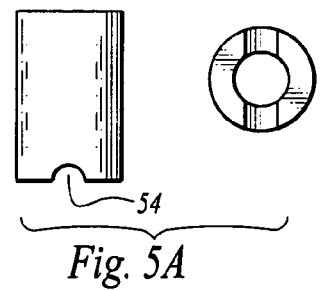
Fig. 5A
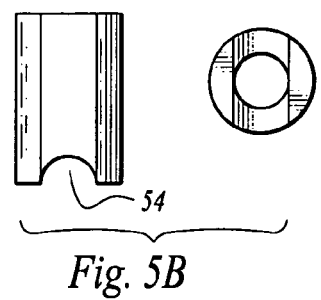
Fig. 5B
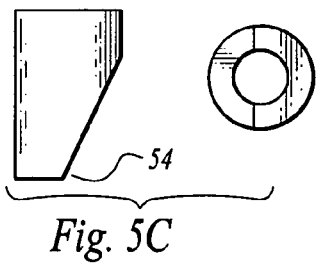
Fig. 5C
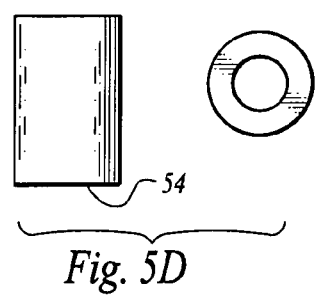
Fig. 5D
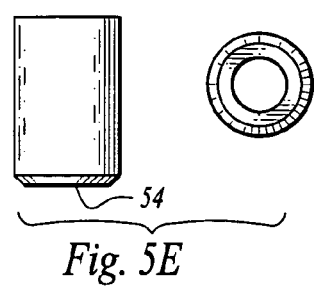
Fig. 5E
Fig. 4

ULTRA LOW VOLUME PROBE

FIELD OF THE INVENTION

The following invention relates generally to devices which transfer liquid. More specifically, the instant invention is directed to a multi-head probe for delivering miniscule volumes of liquid to target sites.

BACKGROUND OF THE INVENTION

One of the most difficult endeavors in the laboratory environment, particularly involving pharmaceuticals, biology, chemistry or medicine, is the placement of minute volumes of liquid onto substrates for subsequent processing. Volumes of liquid in the order of 100 nanoliters or less have negligible weight, are susceptible to ambient fluidic currents, may have an ionic bias and may have surface tension which is large compared to its overall weight. The net effect is that it is extremely difficult to precisely deposit such small volumes on a test plate.

To further complicate the matter, in many laboratory environments, the placement of such small volumes must simultaneously occur a relatively large number of times. For example, multi-probe dispensing heads are known which can dispense simultaneously 48 aliquots, 96 aliquots or even greater numbers at a single instance.

Typically, these multi-probe heads are robotically manipulated and include a large number of needles oriented in an array for simultaneous movement from a loading site to a dispensing site and then to a washing site. Applicant has discovered that one of the factors leading to unreliable liquid transfer, particularly at ultra low volumes includes anomalies that exists with respect to the tips of the needles' location vis-à-vis the underlying surface that is to receive the ultra low volume of liquid. That is to say, when an array of 48, 96 or other number of probes are to contact and deliver an ultra low volume of liquid simultaneously, it is essential that the tips of all the syringe probes contact the receiving surface uniformly in order to assure optimal fluid transfer. If one or more of the needle tips of the probe assembly are not touching the receiving surface, the transfer of liquid can not be assured particularly as to the non-touching tip since the liquid will display an affinity to remain on the tip rather than transfer onto the underlying receiving surface.

SUMMARY OF THE INVENTION

The instant invention assures that each needle tip will make good contact with a surface that is to receive the liquid. Each tip in the probe assembly is capable of independent axial translation when the probe head is docking against the surface to receive the liquid. As a consequence, when the liquid is to be dispensed, each tip is in tangential registry with the underlying receiving surface thus making highly likely that a precise amount of liquid will be left thereon since the surface tension of the liquid is overcome by tangential registry of each needle tip against the underlying surface. Typically the underlying surface is a plate.

A plurality of needles are disposed in an array. Typically the array may be an 8×12 array so that 96 needles are provided, or the array may be a 6×8 array. One end of each needle is attached to tubing that delivers liquid to a tip of the needle remote from the tubing via the needle's central hollow. One end of the needle adjacent the tubing is circumscribed by an upper guide plate in which a hole of the guide plate through which the needle passes is axially aligned with a hole located on a lower guide plate so that the needle can reciprocate along its long axis. The spacing between the upper and lower guide plates is held constant by intervening posts. Interposed between the upper and lower guide plates is a sleeve oriented over each needle and adjacent a top surface of the lower guide plate. Above the sleeve is a spring that is captured between a bottom surface of the upper guide plate and an annular flange located on the needle. Thus the tip of the needle is free to axially reciprocate with respect to the upper and lower guide plates to the extent provided by the spring, the flange, the post, and the sleeve. When all 96 needle tips are placed against a surface, it is desired that all needles will contact the surface simultaneously. To the extent that any of the needles do not contact the surface concurrently with all the needles, the needles' compliance caused by the spring biasing will allow all of the needles to achieve contact with the underlying plate.

This compliant feature also allows the tips of the needles to reside in a relatively shallow pool of liquid during loading of the needles, thereby reducing errors which can occur when liquid clings to an exterior of the needle.

OBJECTS OF THE INVENTION

Accordingly, it is a primary object of the present invention to provide a new, novel and useful instrumentality for delivering ultra low volumes of liquid from a probe head having a multiplicity of fluid outlets.

A further object of the present invention is to provide a device as characterized above which is extremely reliable in use, durable in construction and relatively easy to synchronize into a system.

A further object of the present invention is to provide a method consonant with the above-described objects for the device.

A further object of the present invention is to provide a device and method as characterized above which offsets the effect of the tendency of an ultra low volume of liquid to remain on the tip of the needle.

A further object of the present invention is to provide compliant needles preferably by biasing to assure contact of needle tips with an underlying surface.

These and other objects will be made manifest when considering the following detailed specification when taken in conjunction with the appended drawing figures.

BRIEF DESCRIPTION OF THE DRAWING FIGURES

FIG. 2 is a view of one needle in one extreme position.

FIG. 3 is a view of the same needle in another extreme position.

FIG. 4 is a perspective view of one needle in the probe head in perspective.

Figure 1:
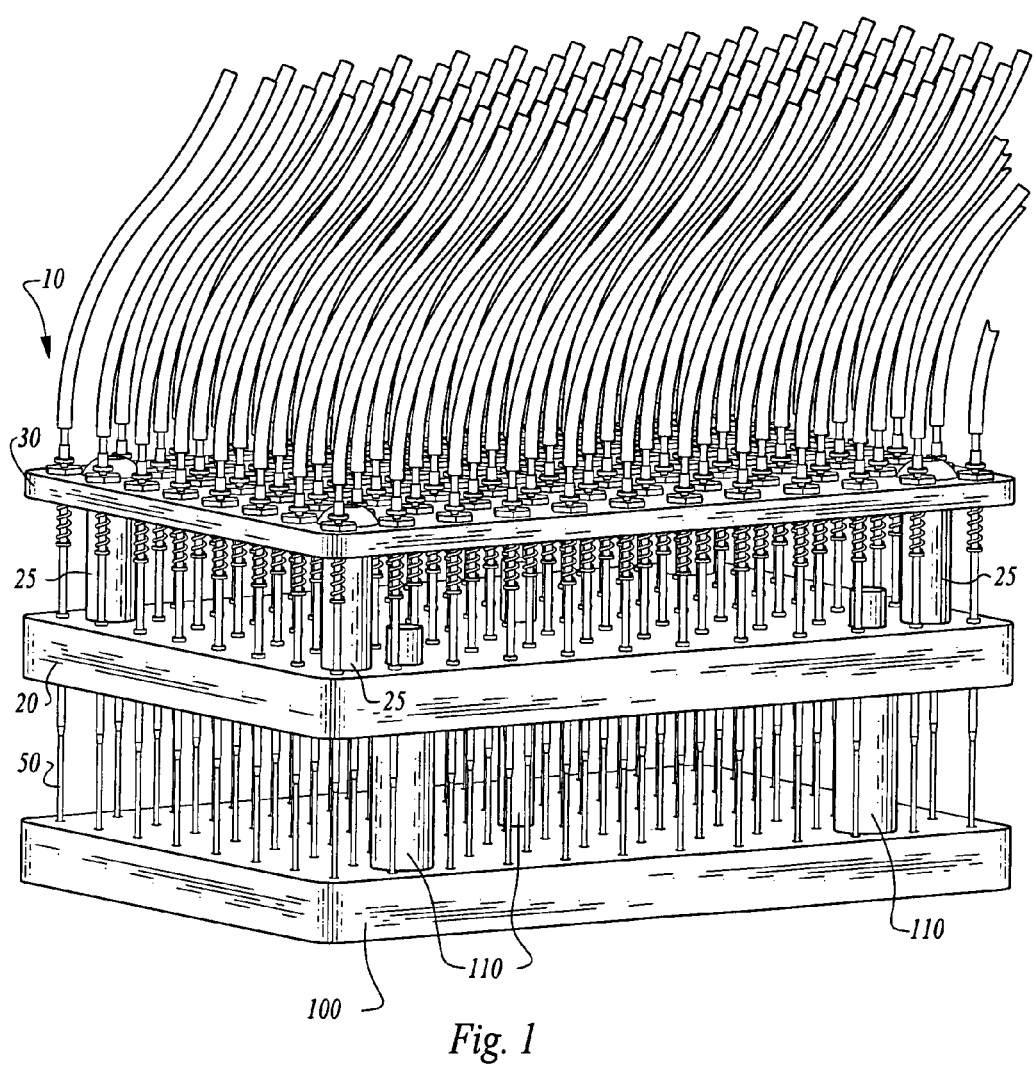
FIG. 1 is a perspective view of the apparatus according to the present invention including a shipping jig that can be used to initialize the multiplicity of needles prior to utilization.

FIGS. 5A–E reflect side and bottoms views of probe tip geometries.

BRIEF DESCRIPTION OF THE PREFERRED EMBODIMENT

Referring to the drawings, wherein like numerals denote like parts, numeral 10 is directed to the probe head according to the present invention. The probe head has a generally rectangular configuration.

As shown in FIG. 1, the probe head 10 is temporarily supported on an underlying jig 100 which includes a plurality of upwardly extending posts 110. The jig 100 and posts 110 elevate a lower support plate 20 of the probe 10. This allows ends of a plurality of needles 50 to depend below plate 20 and either above or on jig 100. The probe head 10 includes an upper support plate 30 fixedly spaced from lower plate 20 by posts 25. The jig 100 is useful to protect needles 50 from damage, particularly during shipping, and to support the probe 10 should replacement of a needle be desired.

As shown in FIG. 1, the probe is substantially a rectangular construct having four posts 25 at the four corners thereof. (The remote corner of FIG. 1 has been obscured by the plurality of needles, but could be visualized in FIG. 4.) Referring to FIG. 4, the needle 50 and its orientation with respect to the upper plate 30 and lower plate 20 can be observed. It can be seen that the spacing between the upper and lower plates 30, 20 is preserved by posts 25 which holds constant this dimension. Post 25 has an upper end 25*a* with a drive socket 25*b*, while its lower end is fixed into lower plate 20.

It can also be observed that the needle 50 includes a free-end 52 having an opening 54 that allows droplets of liquid to be passed there beyond once it has been delivered into the needle by the tube 56 providing a drawing force from an opposite end of the needle 50. In other words, negative pressure created by tube 56 loads the needle at opening 54. Conversely, positive pressure dispenses the liquid. This positive pressure can be enhanced by providing an electrical bias (charge) on the receiving surface 90 (FIG. 4) such as by means of a first polarity (e.g., negative) on surface 90 and a second polarity (e.g., positive) on the tip 52, and vice versa.

A portion immediately up from the needle's lowermost extremity includes a swage 58 configured as a conical taper that leads to a medial body portion 60 having a greater cross sectional diameter than the lower most free end 52. The medial portion 60 passes through the lower plate 20 and is free to reciprocate along the direction of the double ended arrow A as will be explained. The medial portion 60 as it projects above the lower plate 20 is ensconced in a sleeve 62 which preferably has a lower portion press fit into lower plate 20. A spring 64 is dimensioned to ride on top of a flange 72 formed on needle 50 above sleeve 62. The spring 64 constrained in its position by being held in underlying engagement between the lower surface 32 of the upper plate 30 and flange 72. The medial portion 60 extends out from the top surface 34 of the upper plate 30 yielding a free end 66 which frictionally receives the flexible tubing 56 in overlying registry. A bushing 68 removes play from the needle 50 at its upper end 66 while still allowing reciprocation along arrow A. The bushing 68 also permits replacement of needles, since removal of bushing 68 affords clearance for needle substitution.

It can thus be seen that when the tip 54 touches an area to receive a drop of liquid—such as on a sample plate or dish, a downward force in excess of that which is required to induce tangential registry between the tip 54 and plate or dish will cause motion of the needle vertically upward in one direction of the arrow A, opposed by compression of spring 64. Thus, when a multiplicity of such needles are oriented so that all are held in parallel registry, such as in an 8×12 matrix, any needle which first touches the plate or dish which is to receive liquid, will become compliant by moving upwardly along one direction of the double ended arrow A until all needles are in tangential registry with the underlying plate. Once the liquid is pushed from the needle, removal of the probe head from the underlying plate causes needles that had been compressed to move axially down and to be restored to their original position by virtue of the return action by spring 64.

It can thus be seen that it is possible for all needles 50 to contact a receiving surface simultaneously. As a result, a known volume of liquid can be reliably transferred from each needle. FIGS. 5A–E show different geometry for the tip 54. As shown in FIGS. 5A and B, the free end of tip 54 may include an arcuate cutout running diametrically with a width running up to the inner bore (FIG. 5B). FIG. 5C shows a bevel cut while FIG. 5E shows a chamfer which miters and reduces the outlet wall thickness. FIG. 5D shows a flat tip end.

Having thus described the invention, it should be apparent that numerous modifications are to be considered part of this invention, as described hereinabove and as defined by the claims.

The invention claimed is:

1. A probe for dispensing liquid, comprising in combination:
    a plurality of needles supported on a probe head, wherein each said needle includes an upper end, a medial portion, a flange, and a biasing spring;
    a pair of spaced parallel support plates, including an upper plate and a lower plate, wherein said flange is interposed between said support plates, and further, wherein said biasing spring is interposed between said flange and said upper plate; and
    a tube attached to said upper end of each of said needles.

2. The probe of claim 1, further comprising a sleeve located below each said flange, extending above said lower plate, wherein a portion of each said needle is contained within said sleeve.

* * * * *